May 24, 1949. R. L. BYRUM Plant Pat. 839
ROSE PLANT
Filed Sept. 19, 1947
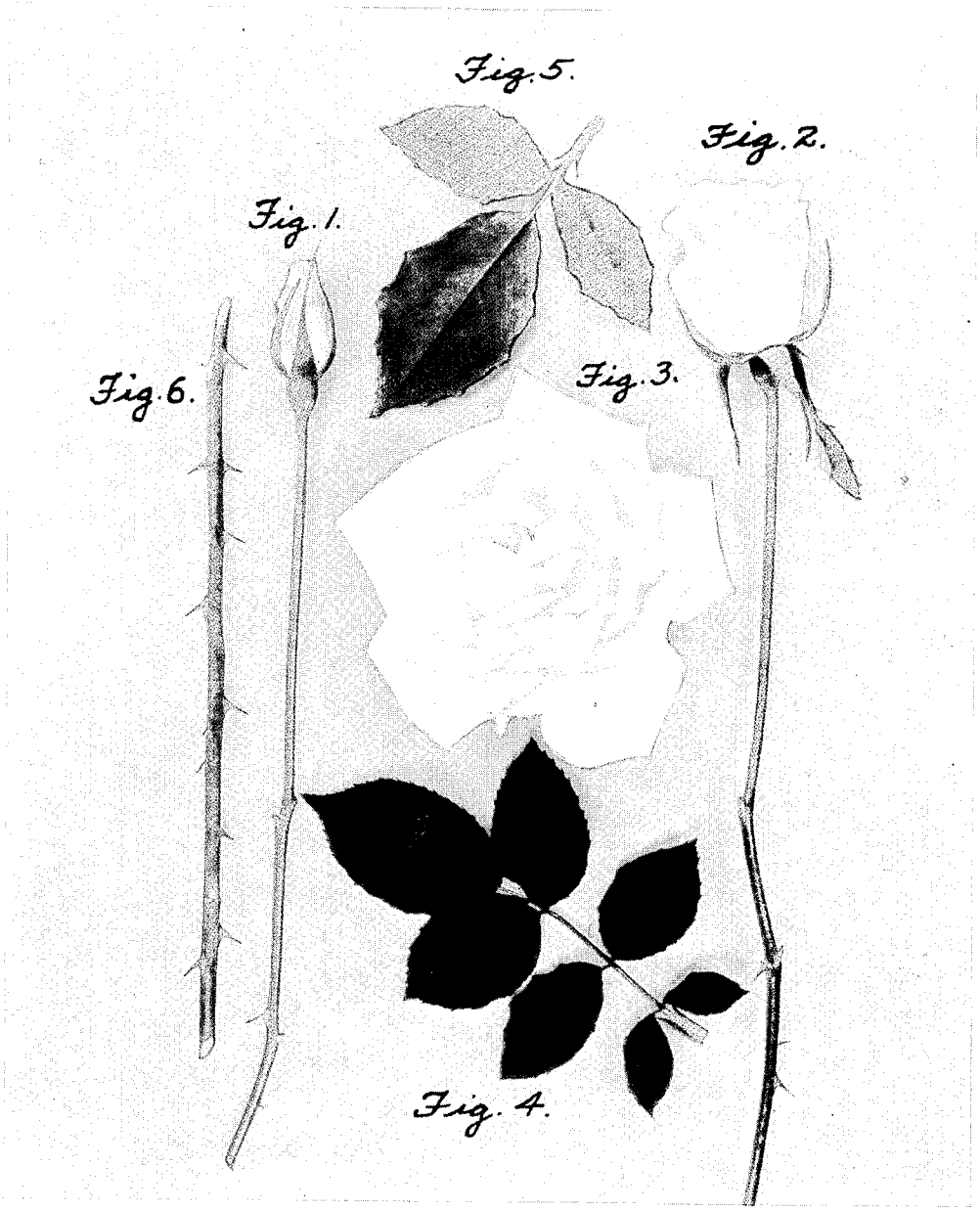
Inventor:
Roy L. Byrum
By: Robb & Robb
Attorneys.

Patented May 24, 1949

Plant Pat. 839

UNITED STATES PATENT OFFICE

839

ROSE PLANT

Roy L. Byrum, Richmond, Ind., assignor to Joseph H. Hill Company, Richmond, Ind., a corporation of Indiana Application September 19, 1947, Serial No. 774,916

1 Claim. (Cl. 47—61)

The present invention relates to a new and distinct variety of rose plant, resulting from a definite effort to secure a rose with the growth and production of the long known variety "Joanna Hill" and the size and color of "R. M. S. Queen Mary" (Pl. Pat. No. 249).

The objectives were reached in the main inasmuch as this new variety in growth is similar to "Joanna Hill," the growth being very free with good production, but the color of the bloom is much darker.

The flowers resemble "R. M. S. Queen Mary" slightly in color, though they are somewhat smaller in size, and the production is better. The bud is quite distinct from either parent, being more pointed, and the plant and flowers, for reasons above mentioned, constitute a desirable improvement in the class of hybrid teas.

Asexual reproduction of this new variety shows the foregoing characteristics come true to form and are established.

In the drawing are shown specimens of the new variety, as follows:

Fig. 1 shows the bud before the calyx breaks;

Fig. 2 is a view corresponding to Fig. 1, as the first petals begin to open;

Fig. 3 shows in plan a newly opened flower showing clearly the arrangement and form of the individual petals;

Fig. 4 is a detail plan of the leaves, a compound of seven;

Fig. 5 the reverse side of a compound of three leaflets; and

Fig. 6 shows a section of the main stem with the form and arrangement of thorns.

The following is a detailed description of the new variety, color terminology being in accord with Ridgway's Color Standard, except where otherwise indicated to have ordinary dictionary significance:

Type: Half hardy; tall; greenhouse; seedling; for cut flowers and garden decoration.

Class: Hybrid tea.

Breeding: Seedling.

*Seed parent.*—"Joanna Hill."

*Pollen parent.*—"R. M. S. Queen Mary."

Propagation: Holds its distinguishing characteristics through succeeding propagations by cutting, grafting and budding. Layering not yet tried.

*Flower*

Locality where grown: Richmond, Indiana.

Flowers borne: Singly to stem on normal, medium long stems.

Quantity of bloom: Abundant outdoors and in greenhouse.

Continuity: Continuous.

Fragrance: Moderate; tea.

Bud:

*Peduncle.*—Medium long; medium heavy; erect; light green; smooth; few green hairs.

*Before calyx breaks.* — *Size* — medium. *Form*—long, pointed, with a conspicuous neck; with foliaceous appendages on the surface of the bud; with slender foliaceous parts extending beyond the tip of the bud equal to one-half or more of its length.

*As calyx breaks.* — *Color* — Begonia Rose, Plate I.

*As first petal opens.*—*Size*—medium large. *Form*—long, pointed. *Color*—outside: Begonia Rose, Plate I; inside: Bittersweet Pink, with shades of Orient Pink mixed in, Plate II.

*Opening.*—Opens up well.

Bloom: Size, when fully open—medium large; three inches to four inches.

*Petalage.*—Semi-double; from 25 to 30 petals arranged regularly.

*Form.*—Globular at first, becoming open; petals remaining at first loosely rolled outward; becoming later, at maturity, very loosely rolled outward.

Petals: Thick, with outside and inside satiny.

*Shape.*—Outside — obovate. Intermediate—obovate. Inside—obovate.

This description of a newly opened flower was made from a rose grown in a greenhouse in the month of November, at Richmond, Indiana:

*Color.*—*Outside petal.*—outside surface: Amber Yellow, Plate XVI, at base, changing to La France Pink, Plate 1, at end of petal; inside surface: Amber Yellow, Plate XVI, at base, changing to La France Pink, Plate 1, at end of petal. *Intermediate petal*—outside surface: Amber Yellow, Plate XVI, at base, changing to Geranium Pink, Plate 1, some petals having yellow streak in center; inside surface: Amber Yellow, Plate XVI, at base, changing to Geranium Pink, Plate 1. *Inner petal*—outside surface: Amber Yellow, Plate XVI, at base, changing to Geranium Pink, Plate 1, some petals having yellow streak in center; inside surface: Amber Yellow, Plate XVI, at base, changing to Geranium Pink, Plate 1.

This description was made from a rose that was open for three days in a greenhouse in the month of November, at Richmond, Indiana:

*Outside petal.*—Outside surface—Amber Yellow, Plate XVI, changing to La France Pink, Plate 1. Inside surface—Amber Yellow, Plate XVI, changing to La France Pink, Plate 1.

*Inside petal.*—Outside surface—Amber Yellow, Plate XVI, changing to La France Pink, Plate 1. Inside surface—Amber Yellow, Plate XVI, changing to La France Pink, Plate 1.

*General color effect.*—Newly opened flower—Eosine Pink, Plate 1. Three days open—Hermosa Pink, Plate 1.

*Behavior*—Persist.

*Flower longevity.*—Cut roses grown in greenhouse, kept at living room temperatures, five to six days in September.

*Reproductive organs*

Stamens: Very many; arranged regularly about pistils.

Filaments: Long; reddish; most with anthers.

Anthers: Medium large; brown; all open at once.

Pollen: Very abundant; yellow.

Pistils: Many.

Styles: Uneven; medium length; thin; bunched.

Stigma: White.

Ovaries: Some protruding from calyx.

Hips: Have not seen any as yet.

Sepals: Permanent; long; spear-shaped.

*Color.*—Inside—Kildare Green, bordered with Absinthe Green, Plate XXXI. Outside—Cress Green, mixed with light Cress Green, Plate XXXI.

*Plant*

Foliage:

*Leaves.*—Compound of five to seven leaflets; abundant; medium large; leathery; wrinkled.

*Leaflets.*—Shape—oval with apex acute. Margin—simply serrate.

*Color.*—*Mature*—upper surface: dark green; under surface: light green. *Young*—upper surface: very light bronze; under surface: very light bronze.

*Rachis.*—Medium heavy. Upper side—grooved; hairy. Under side—prickly.

*Stipules.*—Moderately long; medium wide; with medium long points turning out at an angle of less than 45°.

*Disease.*—Resistant to mildew and blackspot.

Growth:

*Habit.*—Bush; upright; much branched.

*Growth.*—Free.

*Canes.*—Medium heavy.

*Main stems.*—Brown. *Thorns*—several; long; hooked downward; with long base. *Prickles*—none. *Hairs*—none.

*Branches.*—Green. *Thorns*—several; long; hooked downward; with long base. *Prickles*—none. *Hairs*—none.

*New shoots.*—Dull bronze. *Thorns*—several; long; hooked downward; with long base. *Prickles*—none. *Hairs*—none.

I claim:

A new and distinct variety of rose plant, characterized as to novelty by its very free growth; good production of flowers of distinct coloring, substantially as shown and described.

ROY L. BYRUM.

No references cited.